US007723339B2

(12) United States Patent
Brandt et al.

(10) Patent No.: US 7,723,339 B2
(45) Date of Patent: May 25, 2010

(54) COMBINATION COMPRISING A SIGNAL TRANSDUCTION INHIBITOR AND AN EPOTHILONE DERIVATIVE

(75) Inventors: Ralf Brandt, Greenwith (AU); Elisabeth Buchdunger, Neuenburg (DE); Carl-Henrik Heldin, Uppsala (SE); Arne Östman, Uppsala (SE); Kristian Pietras, Uppsala (SE); Terence O'Reilly, Basel (CH); John D Rothermel, Randolph, NJ (US); Peter Traxler, Schonenbuch (CH); Markus Wartmann, Riehen (CH)

(73) Assignee: Novartis AG, Basel (CH)

( * ) Notice: Subject to any disclaimer, the term of this patent is extended or adjusted under 35 U.S.C. 154(b) by 243 days.

(21) Appl. No.: 10/469,367

(22) PCT Filed: Feb. 26, 2002

(86) PCT No.: PCT/EP02/02049

§ 371 (c)(1),
(2), (4) Date: Feb. 18, 2004

(87) PCT Pub. No.: WO02/067941

PCT Pub. Date: Sep. 6, 2002

(65) Prior Publication Data

US 2004/0132754 A1 Jul. 8, 2004

Related U.S. Application Data

(60) Provisional application No. 60/339,040, filed on Oct. 30, 2001.

(30) Foreign Application Priority Data

Feb. 27, 2001 (GB) ................................ 0104840.4

(51) Int. Cl.
*A61K 31/497* (2006.01)
*A61K 31/425* (2006.01)
*A01N 43/78* (2006.01)
*A01N 43/54* (2006.01)
*C07D 239/42* (2006.01)
*C07D 401/04* (2006.01)
*A61K 31/435* (2006.01)
*A01N 43/40* (2006.01)
*A61K 31/505* (2006.01)

(52) U.S. Cl. .................. 514/252.14; 514/365; 514/256; 514/275; 514/277

(58) Field of Classification Search ............ 514/252.14, 514/256, 277, 365, 275
See application file for complete search history.

(56) References Cited

U.S. PATENT DOCUMENTS 6,302,838 B1 * 10/2001 O'Reilly et al. ............. 514/365

FOREIGN PATENT DOCUMENTS

| NZ | 247299 | 7/1995 |
|---|---|---|
| WO | WO 93/10121 | 5/1993 |
| WO | 9702266 | * 1/1997 |
| WO | WO 98/22461 | 5/1998 |
| WO | WO 99/03854 | 1/1999 |

OTHER PUBLICATIONS

Goodman &Gilman's, The Pharmacological Basis of Therapeutics, Ninth Edition, (1996), Calabresi et al., Section X, Chemotherapy of Neoplastic Diseases, pp. 1225-1229.*
STN Database Registry File CAS Registry No. 220127-51-1. Retrieved Nov. 7, 2006. (One Page).*
Bollag, Daniel M. et al., "Epothilones, a new class of microtubule-stabilizing agents with a taxol-like mechanism of action," Cancer Research, vol. 55, pp. 2325-2333 (1995).
Lee, Francis Y.F. et al., "BMS-247550: A novel epothilone analog with a mode of action similar to paclitaxel but possessing superior antitumor efficacy," Clinical Cancer Research, vol. 7, pp. 1429-1437 (2001).
Pietras, Kristian et al., "Inhibition of platelet-derived growth factor receptors reduces interstitial hypertension and increases transcapillary transport in tumors," Cancer Research, vol. 61, pp. 2929-2934 (2001).
UK Search Report, Jun. 8, 2001.
PCT Search Report, May 2, 2003.
Lydon, Nicholas B et al., "A potent protein-tyrosine kinase inhibitor which selectively blocks proliferation of epidermal growth factor receptor-expressing tumor cells in vitro and in vivo," Int. J. Cancer, vol. 76, pp. 154-163 (1998).

* cited by examiner

*Primary Examiner*—Ardin Marschel
*Assistant Examiner*—Leslie A Royds
(74) *Attorney, Agent, or Firm*—George R. Dohmann

(57) ABSTRACT

The present invention relates to a combination comprising N-{5-[4-(4-methyl-piperazino-methyl) -benzoylamido]-2-methylphenyl}-4-(3-pyridyl)-2-pyrimidine-amine and an epothiione derivative; pharmaceutical composition comprising said combination; method of treatment comprising said combination; and commercial packages comprising said combination.

10 Claims, No Drawings

COMBINATION COMPRISING A SIGNAL TRANSDUCTION INHIBITOR AND AN EPOTHILONE DERIVATIVE

The invention relates to a pharmaceutical combination which comprises (a) a signal transduction inhibitor selected from a PDGF (platelet-derived growth factor) receptor tyrosine kinase inhibitor and an active ingredient which decreases the activity of the epidermal growth factor (EGF) and (b) an epothilone derivative of formula I and optionally at least one pharmaceutically acceptable carrier for simultaneous, separate or sequential use, in particular, for the delay of progression or treatment of a proliferative disease, especially a solid tumor disease; a pharmaceutical composition comprising such a combination; the use of such a combination for the preparation of a medicament for the delay of progression or treatment of a proliferative disease; a commercial package or product comprising such a combination as a combined preparation for simultaneous, separate or sequential use, and to a method of treatment of a warm-blooded animal, especially a human.

The phosphorylation of proteins has long been known as an important step in the regulation of the differentiation and proliferation of cells. The phosphorylation is catalysed by protein kinases which are divided into serine/threonine kinases and tyrosine kinases. The PDGF receptor and the EGF receptor belong to the group of receptor tyrosine kinases. STI571 and STI571 B decreases the activity of the PDGF receptor tyrosine kinase. PKI166 and IRESSA™ are examples for compounds that decrease the activity of the EGF.

The microtubule-stabilizing effect of the epothilones was first described by Bollag et al., Cancer Research 55, 1995, 2325-33. A suitable treatment schedule of different types of tumors, especially tumors which are refractory to the treatment by other chemotherapeutics, in particular TAXOL™, is described in WO 99/43320.

Surprisingly, it has now been found that the anti-proliferative effect, i.e. especially the effect in the delay of progression or treatment of a proliferative disease, of a combination as defined herein is greater than the effect that can be achieved with either type of combination partner alone, i.e. greater than the effect of a monotherapy using only one of the combination partners (a) and (b) as defined herein. In particular, it was found that the effect of a combination partner (b) is potentiated in the presence of a PDGF receptor tyrosine kinase inhibitor.

Hence, the present invention pertains to a combination such as a combined preparation or a pharmaceutical composition which comprises (a) a signal transduction inhibitor selected from a PDGF receptor tyrosine kinase inhibitor, especially N-{5-[4-(4-methyl-piperazino-methyl)-benzoylamido]-2-methylphenyl}-4-(3-pyridyl)-2-pyrimidine-amine (STI571) or the monomesylate salt thereof, and an active ingredient which decreases the activity of the epidermal growth factor (EGF), and (b) an epothilone derivative of formula I

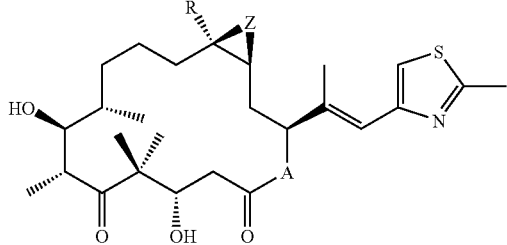

(I)

in which compound A represents O or $NR_N$, wherein $R_N$ is hydrogen or lower alkyl, R is hydrogen or lower alkyl, and Z is O or a bond, in which the active ingredients (a) and (b) are present in each case in free form or in the form of a pharmaceutically acceptable salt and optionally at least one pharmaceutically acceptable carrier; for simultaneous, separate or sequential use.

A compound of formula I wherein A represents O, R is hydrogen and Z is O is known as epothilone A; a compound of formula I wherein A represents O, R is methyl and Z is O is known as epothilone B; a compound of formula I wherein A represents O, R is hydrogen and Z is a bond is known as epothilone C; a compound of formula I wherein A represents O, R is methyl and Z is a bond is known as epothilone D.

The term "a combined preparation", as used herein defines especially a "kit of parts" in the sense that the combination partners (a) and (b) as defined above can be dosed independently or by use of different fixed combinations with distinguished amounts of the combination partners (a) and (b), i.e., simultaneously or at different time points. The parts of the kit can then, e.g., be administered simultaneously or chronologically staggered, that is at different time points and with equal or different time intervals for any part of the kit of parts. Very preferably, the time intervals are chosen such that the effect on the treated disease in the combined use of the parts is larger than the effect which would be obtained by use of only any one of the combination partners (a) and (b) or such that the effect of a combination partner (b) is potentiated due to the presence of a combination partner (a). The ratio of the total amounts of the combination partner (a) to the combination partner (b) to be administered in the combined preparation can be varied, e.g. in order to cope with the needs of a patient sub-population to be treated or the needs of the single patient which different needs can be due to age, sex, body weight, etc. of the patients. Preferably, there is at least one beneficial effect, e.g., a mutual enhancing of the effect of the combination partners (a) and (b), in particular a synergism, e.g. a more than additive effect, additional advantageous effects, less side effects, potentiation, i.e. a combined therapeutical effect in a non-effective dosage of one or both of the combination partners (a) and (b), and very preferably a strong synergism of the combination partners (a) and (b).

The term "delay of progression" as used herein means administration of the combination to patients being in an early phase of the proliferative disease to be treated.

The term "solid tumor disease" as used herein comprises, but is not restricted to glioma, thyroid cancer, breast cancer, ovarian cancer, cancer of the colon and generally the GI tract, cervix cancer, lung cancer, in particular small-cell lung cancer, and non-small-cell lung cancer, head and neck cancer, bladder cancer, cancer of the prostate or Kaposi's sarcoma. In one preferred embodiment of the invention, the tumor disease to be treated is glioma, cancer of the prostate or thyroid cancer. The present combination inhibits the growth of solid tumors, but also liquid tumors. Furthermore, depending on the tumor type and the particular combination used, a decrease of the tumor volume can be obtained. The combinations disclosed herein are also suited to prevent the metastatic spread of tumors and the growth or development of micrometastases.

It will be understood that references to the combination partners (a) and (b) are meant to also include the pharmaceutically acceptable salts. If these combination partners (a) and (b) have, for example, at least one basic center, they can form acid addition salts. Corresponding acid addition salts can also be formed having, if desired, an additionally present basic center. The combination partners (a) and (b) having an acid group (for example COOH) can also form salts with bases. The combination partner (a) or (b) or a pharmaceutically acceptable salt thereof may also be used in form of a hydrate or include other solvents used for crystallization.

Compounds which decrease the activity of the PDGF receptor tyrosine kinase and methods for their preparation are in particular generically and specifically disclosed in the patent applications EP 0 564 409 A1 and WO 99/03853.

Active ingredients which decrease the activity of the EGF are selected from the group consisting of compounds which inhibit the EGE receptor tyrosine kinase, compounds which inhibit the EGF receptor and compounds binding to EGF, and are in particular those compounds generically and specifically disclosed in WO 97/02266, EP 0 564 409, WO 99/03854, EP 0520722, EP 0 566 266, EP 0787 722, EP 0 837063, U.S. Pat. No. 5,747,498, WO 98/10767, WO 97/30034, WO 97/49688, WO 97/38983 and, especially, WO 96/33980. Comprised are likewise the corresponding stereoisomer as well as the corresponding crystal modifications, e.g. solvates and polymorphs, which are disclosed therein. This compounds used as active ingredients in the combinations disclosed herein ca be prepared and administered as described in the cited documents, respectively. In one preferred embodiment of the invention, the employed active ingredient which decreases the activity of the EGF is PKI166, OSI774, C225 (cetuximab), CI-1033, ABX-EGF, EMD-72000, IRESSA™ or MDX-477. In a more preferred embodiment of the invention, the employed active ingredient which decreases the activity of the EGF is PKI166, OSI774, C225 or IRESSA™. Mos preferably, such active ingredient is PKI116 {®-6- (4-hydroxy-phenyl)-4-[(1-phenyl-ethyl)-amino]-&H-pyrrolo[2,3-d]-pyrimidine)}, which is disclosed in WO 97/02266.

Epothilone derivatives of formula I wherein A represents O or $NR_N$, wherein RN is hydrogen or lower alkyl, R is hydrogen or lower alkyl and Z is O or a bond, and methods for the preparation of such epothilone derivatives are in particular generically and specifically disclosed in the patents and patent applications WO 93/10121, U.S. Pat. No. 6,194,181, WO 98/25929, WO 98/08849, WO 99/43653, WO 98/22461 and WO 00/31247. Comprised are likewise the corresponding stereoisomers as well as the corresponding crystal modifications, e.g. solvates and polymorphs, which are disclosed therein.

The transformation of epothilone B to the corresponding lactam is disclosed in Scheme 21 (page 31, 32) and Example 3 of WO 99/02514 (pages 48-50). The transformation of a compound of formula I which is different from epothilone B into the corresponding lactam can be accomplished analogously. Corresponding epothilone derivatives of formula I wherein $R_N$ is lower alkyl can be prepared by methods known in the art such as a reductive alkylation reaction starting from the epothilone derivative wherein $R_N$ is hydrogen.

The structure of the active ingredients identified by code nos., generic or trade names may be taken from the actual edition of the standard compendium "the Merck Index" or from databases, e.g. Patents International (e.g. IMS World Publications). Any person skilled in the art is fully enabled to identify the active ingredients and, based on these references, likewise enabled to manufacture and test the pharmaceutical indications and properties I standard test models, both in vitro and in vivo.

The compounds used as combination partners (a) and (b) disclosed herein can be prepared and administered as described in the cited documents, respectively. PDGF inhibitors of formula II can, for example, be formulated as disclosed in WO 99/03854, especially the monomesylate salt of N-{5-[4-(4-methyl-piperazino-methyl)-benzoylamido]-2-methylphenyl}-4-(3-pyridyl)-2-pyrimidine-amine can be formulated as described in Examples 4 and 6 of WO 99/03854. Epothilone derivatives of formula I, especially epothilone B, can be administered as part of pharmaceutical compositions which are disclosed in WO 99/39694.

A combination which comprises (a) a signal transduction inhibitor selected from a PDGF (platelet-derived growth factor) receptor tyrosine kinase inhibitor and an active ingredient which decreases the activity of the epidermal growth factor (EGF) and (b) an epothilone derivative of formula I in which compound A represents O or $NR_N$, wherein $R_N$ is hydrogen or lower alkyl, R is hydrogen or lower alkyl, and Z is O or a bond, in which the active ingredients are present in each case in free form or in the form of a pharmaceutically acceptable salt and optionally at least one pharmaceutically acceptable carrier, will be referred to hereinafter as a COMBINATION OF THE INVENTION.

The nature of proliferative diseases like solid tumor diseases is multifactorial. Under certain circumstances, drugs with different mechanisms of action may be combined. However, just considering any combination of drugs having different mode of action does not necessarily lead to combinations with advantageous effects.

All the more surprising is the experimental finding that in vivo the administration of a COMBINATION OF THE INVENTION results not only in a beneficial, especially a synergistic therapeutic effect, but also in further surprising beneficial effects, e.g. less than additive side-effects and a decreased mortality and morbidity, compared to a equiefficacious monotherapy applying only one of the pharmaceutically active ingredients used in the COMBINATION OF THE INVENTION. In particular, an increased up-take of the epothilone derivative of formula I in the tumor tissue is observed, when the epothilone derivative of formula I is applied in combination with a PDGF receptor tyrosine kinase inhibitor, especially those disclosed hereinbefore and hereinafter, even if the tumor cells themselves have no PDGF receptors.

A further benefit is that lower doses of the active ingredients of the COMBINATION OF THE INVENTION can be used, for example, that the dosages of at least one combination partner need not only often be smaller, but are also applied less frequently, in order to diminish the incidence of side-effects. This is in accordance with the desires and requirements of the patients to be treated.

It can be shown by established test models and in particular those test models described herein that a COMBINATION OF THE INVENTION results in a more effective delay of progression or treatment of a proliferative disease compared to the effects observed with the single combination partners. The person skilled in the pertinent art is fully enabled to select a relevant test model to prove the hereinbefore and hereinafter mentioned therapeutic indications and beneficial effects. The pharmacological activity of a COMBINATION OF THE INVENTION may, for example, be demonstrated in a clinical study or in a test procedure as essentially described hereinafter.

Suitable clinical studies are in particular open label non-randomized, dose escalation studies in patients with advanced solid tumors. Such studies prove in particular the synergism of the active ingredients of the COMBINATIONS OF THE INVENTION. The beneficial effects on proliferative diseases can be determined directly through the results of these studies or by changes in the study design which are known as such to a person skilled in the art. Such studies are, in particular, suitable to compare the effects of a monotherapy using the active ingredients and a COMBINATION OF THE INVENTION. Preferably, the signal transduction inhibitor is administered with a fixed dose and the dose of the epothilone derivative of formula I, e.g. epothilone B, is escalated until the Maximum Tolerated Dosage is reached.

In a preferred embodiment of the study, each patient receives daily doses of a PDGF receptor tyrosine kinase inhibitor, whereas the epothilone derivative of formula I is administered once weekly i.v. for three weeks, followed by one week off. Each four week interval will be considered one cycle. Day 1 of each cycle is defined as the day of administration of epothilone derivative of formula I and the PDGF receptor tyrosine kinase inhibitor. The efficacy of the treatment can be determined in these studies, e.g., after 18 or 24 weeks by radiologic evaluation of the tumors every 6 weeks. In an alternative embodiment of such a clinical study, the PDGF inhibitor is given as a pretreatment, i.e. before the treatment with the COMBINATION OF THE INVENTION is started, the PDGF inhibitor alone is administered to the patient for a defined period of time, e.g. daily administration of the PDGF inhibitor alone for two or three days.

It is one objective of this invention to provide a pharmaceutical composition comprising a quantity, which is jointly therapeutically effective against a proliferative disease comprising the COMBINATION OF THE INVENTION. In this composition, the combination partners (a) and (b) can be administered together, one after the other or separately in one combined unit dosage form or in two separate unit dosage forms. The unit dosage form may also be a fixed combination.

The pharmaceutical compositions according to the invention can be prepared in a manner known per se and are those suitable for enteral, such as oral or rectal, and parenteral administration to mammals (warm-blooded animals), including man, comprising a therapeutically effective amount of at least one pharmacologically active combination partner alone or in combination with one or more pharmaceutically acceptable carries, especially suitable for enteral or parenteral application.

The novel pharmaceutical composition contain, for example, from about 10% to about 100%, preferably from about 20% to about 60%, of the active ingredients. Pharmaceutical preparations for the combination therapy for enteral or parenteral administration are, for example, those in unit dosage forms, such as sugar-coated tablets, tablets, capsules or suppositories, and furthermore ampoules. If not indicated otherwise, these are prepared in a manner known per se, for example by means of conventional mixing, granulating, sugar-coating, dissolving or lyophilizing processes. It will be appreciated that the unit content of a combination partner contained in an individual dose of each dosage form need not in itself constitute an effective amount since the necessary effective amount can be reached by administration of a plurality of dosage units.

In preparing the compositions for oral dosage form, any of the usual pharmaceutical media may be employed, such as, for example, water, glycols, oils, alcohols, flavoring agents, preservatives, coloring agents; or carriers such as starches, sugars, microcristalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed.

In particular, a therapeutically effective amount of each of the combination partner of the COMBINATION OF THE INVENTION may be administered simultaneously or sequentially and in any order, and the components may be administered separately or as a fixed combination. For example, the method of delay of progression or treatment of a proliferative disease according to the invention may comprise (I) administration of the first combination partner in free or pharmaceutically acceptable salt form and (ii) adminstration of the second combination partner in free or pharmaceutically acceptable salt form, simultaneously or sequentially in any order, in jointly therapeutically effective amounts, preferably in synergistically effective amounts, e.g. in daily or weekly dosages corresponding to the amounts described herein. The individual combination partners of the COMBINATION OF THE INVENTION can be administered separately at different times during the course of therapy or concurrently in divided or single combination forms. Furthermore, the term administering also encompasses the use of a pro-drug of a combination partner that convert in vivo to the combination partner as such. The instant invention is therefore to be understood as embracing all such regimes of simultaneous or alternating treatment and the term "administering" is to be interpreted accordingly.

The effective dosage of each of the combination partners employed in the COMBINATION OF THE INVENTION may vary depending on the particular compound or pharmaceutical composition employed, the mode of administration, the condition being treated, the severity of the condition being treated. Thus, the dosage regimen for the COMBINATION OF THE INVENTION is selected in accordance with a variety of factors including the route of administration and the renal and hepatic function of the patient. A physician, clinician or veterinarian of ordinary skill can readily determine and prescribe the effective amount of the single active ingredients required to prevent, counter or arrest the progress of the condition. Optimal precision in achieving concentration of the active ingredients within the range that yields efficacy without toxicity requires a regimen based on the kinetics of the active ingredients' availability to target sites. This involves a consideration of the distribution, equilibrium, and elimination of the active ingredients.

When the combination partners employed in the COMBINATION OF THE INVENTION are applied in the form as marketed as single drugs, their dosage and mode of administration can take place in accordance with the information provided on the packet leaflet of the respective marketed drug in order to result in the beneficial effect described herein, if not mentioned herein otherwise.

If the the warm-blooded animal is a human, the dosage of a compound of formula I is preferably in the range of about 0.25 to 75, preferably 0.5 to 50, e.g. 2.5, mg/m$^2$ once weekly for two to four, e.g. three, weeks, followed by 6 to 8 days off in the case of an adult patient. In one embodiment of the invention, epothilone B is administered in accordance with the treatment schedule described in U.S. Pat. No. 6,302,838 which disclosure is enclosed herein by reference.

Unless stated otherwise herein, the PDGF receptor tyrosine kinase inhibitors are preferably administered from one to four times per day. Furthermore, the PDGF receptor tyrosine kinase inhibitors, especially N-{5-[4-(4-methyl-piperazino-methyl)-benzoylamido]-2-methylphenyl}-4-(3-pyridyl)-2-pyrimidine-amine monomesylate, are preferably administered to the warm-blooded animal in a dosage in the range of about 2.5 to 1000 mg/day, more preferably 5 to 750 mg/day and most preferably 25 to 300 mg/day, e.g. 100 mg or 200 mg/day, when the warm-blooded animal is a human.

The dosage of PKI166, if employed, is preferably in the range of about 50 to 700, more preferably about 100 to 500, and most preferably about 150 to 300, mg/day. In one embodiment the present invention PKI166 is administered to the human subject less frequently than on a daily basis. In particular, a treatment regimen is employed wherein over at least a three week period PKI166 is administered on only about 40% to about 71% of the days.

Unless stated otherwise, in the present disclosure organic radicals and compounds designated "lower" contain not more than 7, preferably not more than 4, carbon atoms.

In a preferred embodiment of the invention, the COMBINATION OF THE INVENTION comprises (a) a PDGF receptor tyrosine kinase inhibitor which is a N-phenyl-2-pyrimidine-amine derivative of formula II,

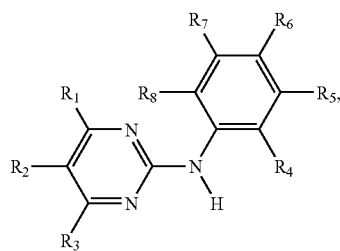

(II)

wherein $R_1$ is 4-pyrazinyl; 1-methyl-1H-pyrrolyl; amino- or amino-lower alkyl-substituted phenyl, wherein the amino group in each case is free, alkylated or acylated; 1H-indolyl or 1H-imidazolyl bonded at a five-membered ring carbon atom; or unsubstituted or lower alkyl-substituted pyridyl bonded at a ring carbon atom and unsubstituted or substituted at the nitrogen atom by oxygen; $R_2$ and $R_3$ are each independently of the other hydrogen or lower alkyl; one or two of the radicals $R_4$, $R_5$, $R_6$, $R_7$ and $R_8$ are each nitro, fluoro-substituted lower alkoxy or a radical of formula III

—N($R_9$)—C(=X)—(Y)$_n$—$R_{10}$    (III), wherein $R_9$ is hydrogen or lower alkyl, X is oxo, thio, imino, N-lower alkyl-imino, hydroximino or O-lower alkyl-hydroximino, Y is oxygen or the group NH, n is 0 or 1 and $R_{10}$ is an aliphatic radical having at least 5 carbon atoms, or an aromatic, aromatic-aliphatic, cycloaliphatic, cycloaliphatic-aliphatic, heterocyclic or heterocyclic-aliphatic radical, and the remaining radicals $R_4$, $R_5$, $R_6$, $R_7$ and $R_8$ are each independently of the others hydrogen, lower alkyl that is unsubstituted or substituted by free or alkylated amino, piperazinyl, piperidinyl, pyrrolidinyl or by morpholinyl, or lower alkanoyl, trifluoromethyl, free, etherified or esterifed hydroxy, free, alkylated or acylated amino or free or esterified carboxy, and (b) an epothilone derivative of formula I in which compound A represents O or $NR_N$, wherein $R_N$ is hydrogen or lower alkyl, R is hydrogen or lower alkyl, and Z is O or a bond, in which the active ingredients are present in each case in free form or in the form of a pharmaceutically acceptable salt and optionally at least one pharmaceutically acceptable carrier.

1-Methyl-1H-pyrrolyl is preferably 1-methyl-1H-pyrrol-2-yl or 1-methyl-1H-pyrrol-3-yl.

Amino- or amino-lower alkyl-substituted phenyl $R_1$ wherein the amino group in each case is free, alkylated or acylated is phenyl substituted in any desired position (ortho, meta or para) wherein an alkylated amino group is preferably mono- or di-lower alkylamino, for example dimethylamino, and the lower alkyl moiety of amino-lower alkyl is preferably linear $C_1$-$C_3$alkyl, such as especially methyl or ethyl.

1H-Indolyl bonded at a carbon atom of the five-membered ring is 1H-indol-2-yl or 1H-indol-3-yl.

Unsubstituted or lower alkyl-substituted pyridyl bonded at a ring carbon atom is lower alkyl-substituted or preferably unsubstituted 2-, 4- or preferably 3-pyridyl, for example 3-pyridyl, 2-methyl-3-pyridyl or 4-methyl-3-pyridyl. Pyridyl substituted at the nitrogen atom by oxygen is a radical derived from pyridine N-oxide, i.e. N-oxido-pyridyl.

Fluoro-substituted lower alkoxy is lower alkoxy carrying at least one, but preferably several, fluoro substituents, especially trifluoromethoxy or 1,1,2,2-tetrafluoro-ethoxy.

When X is oxo, thio, imino, N-lower alkyl-imino, hydroximino or O-lower alkyl-hydroximino, the group C=X is, in the above order, a radical C=O, C=S, C=N—H, C=N-lower alkyl, C=N—OH or C=N—O-lower alkyl, respectively. X is preferably oxo.

n is preferably 0, i.e. the group Y is not present.

Y, if present, is preferably the group NH.

Lower alkyl $R_1$, $R_2$, $R_3$ and $R_9$ is preferably methyl or ethyl.

An aliphatic radical $R_{10}$ having at least 5 carbon atoms preferably has not more than 22 carbon atoms, generally not more than 10 carbon atoms, and is such a substituted or preferably unsubstituted aliphatic hydrocarbon radical, that is to say such a substituted or preferably unsubstituted alkynyl, alkenyl or preferably alkyl radical, such as $C_5$-$C_7$alkyl, for example n-pentyl. An aromatic radical $R_{10}$ has up to 20 carbon atoms and is unsubstituted or substituted, for example in each case unsubstituted or substituted naphthyl, such as especially 2-naphthyl, or preferably phenyl, the substituents preferably being selected from cyano, unsubstituted or hydroxy-, amino- or 4-methyl-piperazinyl-substituted lower alkyl, such as especially methyl, trifluoromethyl, free, etherified or esterified hydroxy, free, alkylated or acylated amino and free or esterified carboxy. In an aromatic-aliphatic radical $R_{10}$ the aromatic moiety is as defined above and the aliphatic moiety is preferably lower alkyl, such as especially $C_1$-$C_2$alkyl, which is substituted or preferably unsubstituted, for example benzyl. A cycloaliphatic radical $R_{10}$ has especially up to 30, more especially up to 20, and most especially up to 10 carbon atoms, is mono- or poly-cyclic and is substituted or preferably unsubstituted, for example such a cycloalkyl radical, especially such a 5- or 6-membered cycloalkyl radical, such as preferably cyclohexyl. In a cycloaliphatic-aliphatic radical $R_{10}$ the cycloaliphatic moiety is as defined above and the aliphatic moiety is preferably lower alkyl, such as especially $C_1$-$C_2$alkyl, which is substituted or preferably unsubstituted. A heterocyclic radical $R_{10}$ contains especially up to 20 carbon atoms and is preferably a saturated or unsaturated monocyclic radical having 5 or 6 ring members and 1-3 hetero atoms which are preferably selected from nitrogen, oxygen and sulfur, especially, for example, thienyl or 2-, 3- or 4-pyridyl, or a bi- or tri-cyclic radical wherein, for example, one or two benzene radicals are annellated (fused) to the mentioned monocyclic radical. In a heterocyclic-aliphatic radical $R_{10}$ the heterocyclic moiety is as defined above and the aliphatic moiety is preferably lower alkyl, such as especially $C_1$-$C_2$alkyl, which is substituted or preferably unsubstituted.

Etherified hydroxy is preferably lower alkoxy. Esterified hydroxy is preferably hydroxy esterified by an organic carboxylic acid, such as a lower alkanoic acid, or a mineral acid, such as a hydrohalic acid, for example lower alkanoyloxy or especially halogen, such as iodine, bromine or especially fluorine or chlorine.

Alkylated amino is, for example, lower alkylamino, such as methylamino, or di-lower alkyl-amino, such as dimethylamino. Acylated amino is, for example, lower alkanoylamino or benzoylamino.

Esterified carboxy is, for example, lower alkoxycarbonyl, such as methoxycarbonyl.

A substituted phenyl radical may carry up to 5 substituents, such as fluorine, but especially in the case of relatively large substituents is generally substituted by only from 1 to 3 substituents. Examples of substituted phenyl that may be given special mention are 4-chloro-phenyl, pentafluoro-phenyl, 2-carboxy-phenyl, 2-methoxy-phenyl, 4-fluoro-phenyl, 4-cyano-phenyl and 4-methyl-phenyl.

Salt-forming groups in a compound of formula I are groups or radicals having basic or acidic properties. Compounds having at least one basic group or at least one basic radical, for example a free amino group, a pyrazinyl radical or a pyridyl radical, may form acid addition salts, for example with inorganic acids, such as hydrochloric acid, sulfuric acid or a phosphoric acid, or with suitable organic carboxylic or sulfonic acids, for example aliphatic mono- or di-carboxylic acids, such as trifluoroacetic acid, acetic acid, propionic acid, glycolic acid, succinic acid, maleic acid, fumaric acid, hydroxymaleic acid, malic acid, tartaric acid, citric acid or oxalic acid, or amino acids such as arginine or lysine, aromatic carboxylic acids, such as benzoic acid, 2-phenoxy-benzoic acid, 2-acetoxy-benzoic acid, salicylic acid, 4-aminosalicylic acid, aromatic-aliphatic carboxylic acids, such as mandelic acid or cinnamic acid, heteroaromatic carboxylic acids, such as nicotinic acid or isonicotinic acid, aliphatic sulfonic acids, such as methane-, ethane- or 2-hydroxy-ethane-sulfonic acid, or aromatic sulfonic acids, for example benzene-, p-toluene- or naphthalene-2-sulfonic acid. When several basic groups are present mono- or poly-acid addition salts may be formed.

Compounds of formula II having acidic groups, for example a free carboxy group in the radical $R_{10}$, may form metal or ammonium salts, such as alkali metal or alkaline earth metal salts, for example sodium, potassium, magnesium or calcium salts, or ammonium salts with ammonia or suitable organic amines, such as tertiary monoamines, for example triethylamine or tri-(2-hydroxyethyl)-amine, or heterocyclic bases, for example N-ethyl-piperidine or N,N'-dimethyl-piperazine.

Compounds of formula II having both acidic and basic groups can form internal salts.

For the purposes of isolation or purification, as well as in the case of compounds that are used further as intermediates, it is also possible to use pharmaceutically unacceptable salts. Only pharmaceutically acceptable, non-toxic salts are used for therapeutic purposes, however, and those salts are therefore preferred.

Preferably, such COMBINATION OF THE INVENTION comprises a PDGF receptor tyrosine kinase inhibitor of formula II, wherein $R_1$ is pyridyl or N-oxido-pyridyl each of which is bonded at a carbon atom, $R_2$ and $R_3$ are each hydrogen, $R_4$ is hydrogen or lower alkyl, $R_5$ is hydrogen, lower alkyl or trifluoromethyl, $R_6$ is hydrogen, $R_7$ is nitro, fluoro-substituted lower alkoxy or a radical of formula III wherein $R_9$ is hydrogen, X is oxo, n is 0 and $R_{10}$ is pyridyl bonded at a carbon atom, phenyl that is unsubstituted or substituted by halogen, cyano, lower alkoxy, carboxy, lower alkyl or by 4-methyl-piperazinyl-methyl, or $C_5$-$C_7$alkyl, thienyl, 2-naphthyl or cyclohexyl, and $R_8$ is hydrogen.

More preferably, in a PDGF receptor tyrosine kinase inhibitor of formula II $R_1$ is pyridyl bonded at a carbon atom, $R_2$, $R_3$, $R_5$, $R_6$ and $R_8$ are each hydrogen, $R_4$ is lower alkyl, $R_7$ a radical of formula III wherein $R_9$ is hydrogen, X is oxo, n is 0 and $R_{10}$ is 4-methyl-piperazinyl-methyl.

Even more preferred is a COMBINATION OF THE INVENTION comprising (a) a PDGF receptor tyrosine kinase inhibitor of formula II, which is N-{5-[4-(4-methyl-piperazino-methyl)-benzoylamido]-2-methylphenyl}-4-(3-pyridyl)-2-pyrimidine-amine, most preferably in the form of its monomesylate salt, and (b) an epothilone derivative of formula I in which compound A represents O or $NR_N$, wherein $R_N$ is hydrogen or lower alkyl, R is hydrogen or lower alkyl, and Z is O or a bond, in which the active ingredients are present in each case in free form or in the form of a pharmaceutically acceptable salt and optionally at least one pharmaceutically acceptable carrier.

In the compound of formula I preferably A represents O. R is lower alkyl, e.g. ethyl or, most preferably, methyl. Z is preferably O.

In one preferred embodiment of the invention the COMBINATION OF THE INVENTION comprises STI571 and epothilone B. In a further preferred embodiment of the invention the COMBINATION OF THE INVENTION comprises PKI166 and epothilone B.

The COMBINATION OF THE INVENTION can be a combined preparation or a pharmaceutical composition.

Moreover, the present invention relates to a method of treating a warm-blooded animal having a proliferative disease comprising administering to the animal a COMBINATION OF THE INVENTION in a quantity which is jointly therapeutically effective against a proliferative disease and in which the combination partners can also be present in the form of their pharmaceutically acceptable salts.

Furthermore, the present invention pertains to the use of a COMBINATION OF THE INVENTION for the delay of progression or treatment of a proliferative disease and for the preparation of a medicament for the delay of progression or treatment of a proliferative disease.

Additionally, the present invention relates to the use of a compound which decreases the activity of the PDGF receptor tyrosine kinase in combination with an epothilone derivative of formula I in which compound A represents O or $NR_N$, wherein $R_N$ is hydrogen or lower alkyl, R is hydrogen or lower alkyl, and Z is O or a bond, especially for the preparation of a medicament for the delay of progression or treatment of a proliferative disease.

Moreover, the present invention provides a commercial package comprising as active ingredients COMBINATION OF THE INVENTION, together with instructions for simultaneous, separate or sequential use thereof. In the delay of progression or treatment of a proliferative disease.

In one embodiment of the invention, an antidiarrheal agent is administered together with the COMBINATION OF THE INVENTION in order to prevent, control or eliminate diarrhea that is sometimes associated with the administration of epothilones, especially epothilone B. Thus, the present invention also relates to a method of preventing or controlling diarrhea associated with administering an epothilone derivative of formula I, which comprises administering an effective amount of an antidiarrhea agent to the patient receiving treatment with the COMBINATION OF THE INVENTION. Antidiarrheal agents and protocols for their administration are known to those skilled in the art. Antidiarrheal agents suitable for use in the inventive methods and compositions include, but are not limited to, natural opiods, such as tincture of opium, paregoric, and codeine, synthetic opioids, such as diphenoxylate, difenoxin and loperamide, bismuth subsalicylate, octreotide (e.g. available as SANDOSTATIN™), motilin antagonists and traditional antidiarrheal remedies, such as kaolin, pectin, berberine and muscarinic agents.

The following Examples illustrate the invention described above; they are not, however, intended to limit the scope of the invention in any way. The beneficial effects of the COMBI- NATION OF THE INVENTION can also be determined by other test models known as such to the person skilled in the pertinent art.

EXAMPLE 1

STI571 Alone, Epothilone B (EPO906) Alone and the Combination of STI571 Plus Epothilone B Versus Rat C6 Glioma Tumor Xenografts in Female BALB/C Mice Tumors are initiated by the s.c. injection of $1\times10^6$ rat C6 cells (n=8/group). When the tumors reaches ~75 mm$^3$, STI571 treatment is begun at 200 mg/kg, p.o., q24h. The combination partner epothilone B is administered on days 3 and 10 at 1 or 2 mg/kg, i.v. The observed Delta tumor volumes (mean mm$^3$±SEM) are as follows: Control: 1289±178, STI571 200 mg/kg, p.o., q24h: 883±169, EPO906 2 mg/kg, q7d: 419±116, EPO906 1 mg/kg, q7d: 864±115, STI571 200 mg/kg, p.o., q24h plus EPO906 2 mg/kg, q7d: 122±61, STI571 200 mg/kg, p.o., q24h plus EPO906 1 mg/kg, q7d: 598±112.

The analysis of the results indicates a trend for synergy of STI571 and EPO906: EPO906/controls=0.325; STI571/controls=0.685; EPO906 plus STI571/controls=0.095. As EPO906 plus STI571/controls<EPO906/controls×STI571/controls, this is defined as synergy (Clark, Br. Can. Res. Treat. 1997, 46, 255).

Furthermore, body weight loss is not additive when employing the combination of STI571 plus epothilone B.

EXAMPLE 2

Study on the Effects of Combining Epothilone B Treatment of KAT-4 Mouse Thyroid Carcinoma with Treatment with STI571

KAT-4 tumors are established in SCID mice by subcutaneous injection of $2\times10^6$ tumor cells. Treatment studies are initiated when tumors have reached a size of 50-150 mm$^3$. Epothilone B is administered s.c. once weekly. STI571, at a dose of 100 mg/kg, is administered by gavage and given once daily. Tumor volume is determined by mesurements with calipers.

In the study four groups of tumor bearing mice are analyzed: control treated mice, mice treated with either STI571 (100 mg/kg) or 0.3 mg/kg of EPO906 alone and mice treated with both drugs. Treatment is performed on mice with an average starting size of tumor of approximatly 100 mm$^3$. EPO906 is given at days 6, 13 and 20 and STI571 is given once daily from day 3. No reduction in body-weight is observed in animals receiving the combination treatment. Results: Treatment with STI571 alone has no effect of tumor growth. Treatment with 0.3 mg/kg of EPO906 gives a statistically significant reduction of tumor growth leading to final tumor size corresponding to 69% of control tumors. The tumors of combination-treated animals display statistically significantly slower growth as compared to the tumors of mice that receive treatment with EPO906 alone. At the end of the experiment the size of tumors from the combination-treated mice is only 45% of the size of the control treated animals.

By such Example it is shown that the PDGF-R inhibitor STI571 potentiates the anti-tumor effect of epothilone B in vivo, whereas the toxicity is unaffected.

What is claimed is:

1. A method of treating a warm-blooded animal having a proliferative disease comprising administering to the animal a combination of (a) N-{5-[4-(4-methyl-piperazino-methyl)-benzoylamido]-2-methylphenyl}-4-(3-pyridyl)-2-pyrimidine-amine; and (b) an epothilone, of formula I

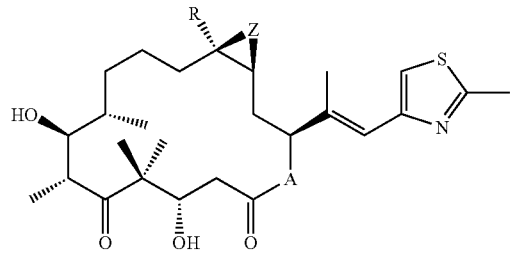

in which A represents O or NR$_N$, wherein R$_N$ is hydrogen or lower alkyl, R is hydrogen or lower alkyl, and Z is O, in which the active ingredients (a) and (b) are present in each case in free form or in the form of a pharmaceutically acceptable salt and optionally at least one pharmaceutically acceptable carrier; for simultaneous, separate or sequential use, in a quantity which is jointly therapeutically effective against a proliferative disease wherein the proliferative disease is selected from the group consisting of glioma and thyroid carcinoma.

2. A method of claim 1 wherein A is O.
3. A method of claim 1 wherein A is NR$_N$.
4. A method of claim 2 wherein R is methyl.
5. A method of claim 4 wherein the proliferative disease is glioma.
6. A method of claim 4 wherein the proliferative disease is thyroid carcinoma.
7. A method of claim 5 wherein (a) is in the form of a pharmaceutically acceptable salt.
8. A method of claim 7 wherein the pharmaceutically acceptable salt is the monomesylate salt.
9. A method of claim 6 wherein (a) is in the form of a pharmaceutically acceptable salt.
10. A method of claim 9 wherein the pharmaceutically acceptable salt is the monomesylate salt.

* * * * *